United States Patent [19]

Dunn

[11] Patent Number: 5,038,777
[45] Date of Patent: Aug. 13, 1991

[54] ENDOTRACHEAL DEVICE

[76] Inventor: Margarette T. Dunn, 2421 Dartmouth Dr., Fayetteville, N.C. 28304

[21] Appl. No.: 669,689

[22] Filed: Mar. 14, 1991

[51] Int. Cl.$^5$ ............................................. A62B 9/00
[52] U.S. Cl. ............................................. 128/207.14
[58] Field of Search ................ 128/207.15, 207.14; 604/99, 101

[56] References Cited

U.S. PATENT DOCUMENTS

| | | |
|---|---|---|
| 2,210,744 | 8/1940 | Winder . |
| 3,173,418 | 3/1965 | Baran . |
| 3,211,152 | 10/1965 | Stern . |
| 3,889,688 | 6/1975 | Eamkaow ............................ 128/351 |
| 3,931,822 | 1/1976 | Marici ................................. 128/351 |
| 4,018,231 | 4/1977 | Wallace ............................ 128/207.15 |
| 4,141,364 | 2/1979 | Schultze ........................... 128/207.15 |
| 4,791,923 | 12/1988 | Shapiro ............................ 128/207.15 |
| 4,834,087 | 5/1989 | Coleman et al. ................. 128/207.14 |

*Primary Examiner*—Edgar S. Burr
*Assistant Examiner*—Lisa E. Malvaso

[57] ABSTRACT

An endotracheal device includes an outer inflatable cuff and an inner furled cuff for use in emergency conditions. The secondary or furled cuff is formed from a resilient, stretchable polymeric material which allows the cuff to be quickly inflated during use and after use, upon release of the air pressure within, quickly reverts to its tightly wrapped position around the endotracheal tube whereby the endotracheal device can be easily and conveniently removed from the patient. Fluid conduits are provided to inflate both the primary and secondary cuffs independently.

10 Claims, 1 Drawing Sheet

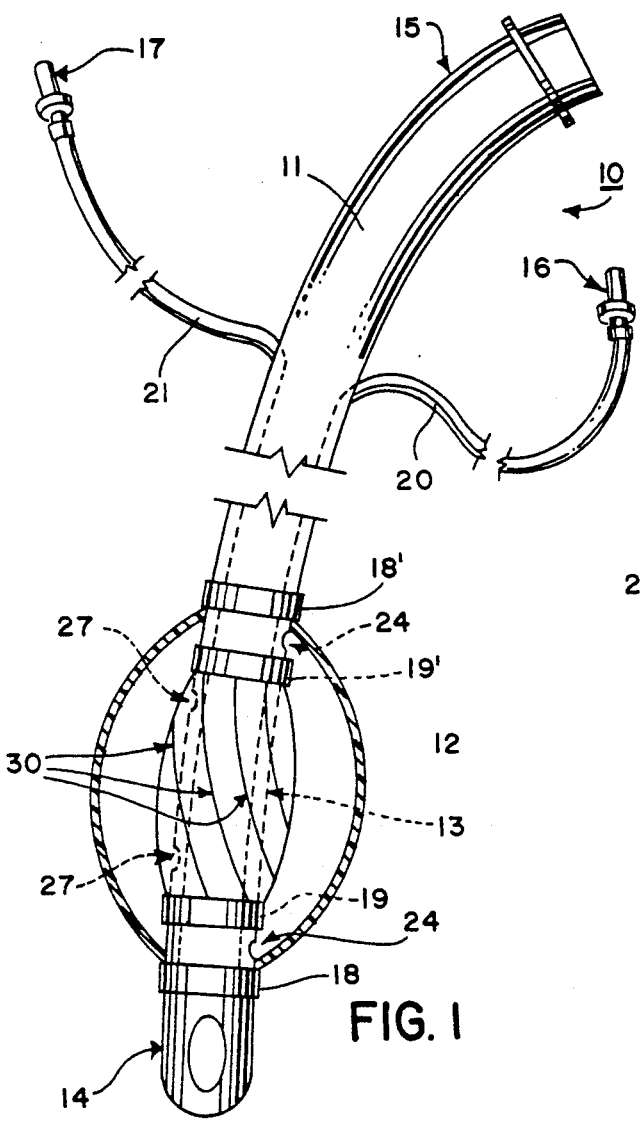
FIG. 1
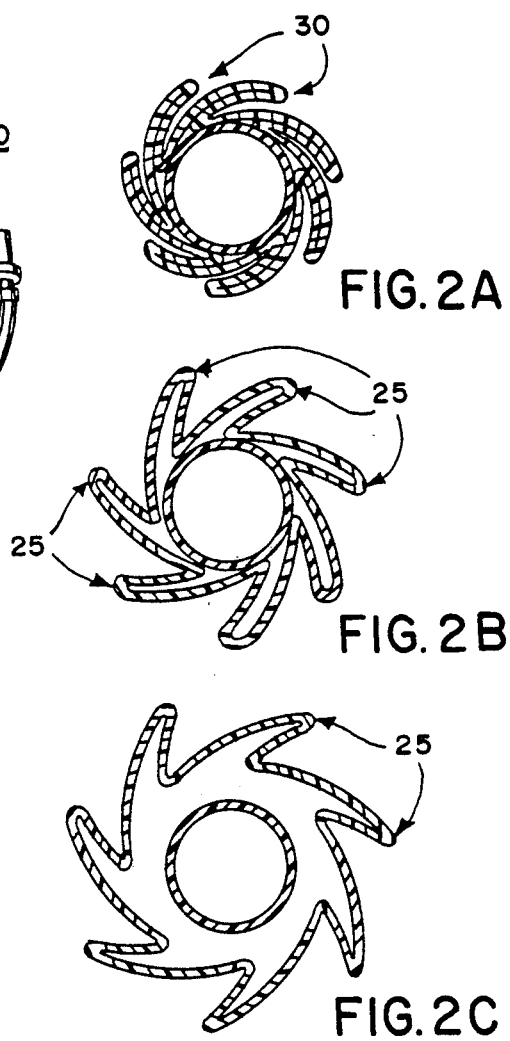
FIG. 2A
FIG. 2B
FIG. 2C
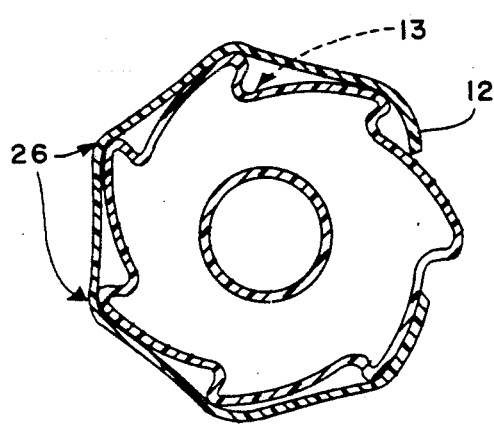
FIG. 3
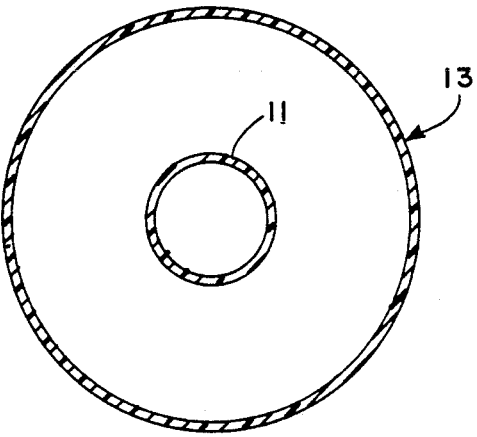
FIG. 2D

ENDOTRACHEAL DEVICE

BACKGROUND OF THE INVENTION

1. Field of the Invention

The invention herein relates to endotracheal tubes for use with patients undergoing anesthesia, surgery or mechanical ventilation.

2. Description Of The Prior Art And Objectives Of The Invention

Various endotracheal tubes have been conceived in the past utilizing cuffs or bulbs which are expanded or inflated by the use of a catheter. The inflated cuff will contact and seal the tracheal walls during anesthesia or the like to prevent aspiration of gastric or oral contents or the escape of air. Certain prior art endotracheal tubes have utilized a pair of cuffs or bulbs and in particular, U.S. Pat. No. 3,211,152 utilizes an inner and outer bulb for safety purposes. The double cuff endotracheal tubes thereby allow a second cuff to be inflated, upon rupture of the first cuff, to prevent aspiration and air leakage during ventilation.

While such prior art endotracheal tubes utilizing double cuffs are useful, problems have been known to arise due to the bulk of one cuff inside another. For example, during a trial inflation before insertion, the inner or secondary cuff may not fully deflate or reposition itself exactly and can cause additional diameter or "bulk" to the elongated endotracheal tube. This additional bulk can cause difficulty in inserting the endotracheal tube, such as during passage through the nostrils.

Therefore, with the limitations and disadvantages of known endotracheal tubes, the present invention was conceived and one of its objectives is to provide a safe, easily insertable endotracheal tube which includes a primary and a secondary inner inflatable cuff.

It is another objective of the present invention to provide an endotracheal tube having a secondary cuff which is tightly and compactly positioned on the endotracheal tube for ease during insertion and extraction.

It is yet another objective of the present invention to provide a secondary cuff which is tightly furled around the endotracheal tube prior to inflation and which will return to its pre-inflation position when deflated.

It is yet another objective of the present invention to provide an endotracheal tube which includes independent means to inflate each of said primary and secondary cuffs.

Various other objectives and advantages of the present invention become apparent to those skilled in the art as a more detailed presentation is set forth below.

SUMMARY OF THE INVENTION

The aforesaid and other objectives are realized by an endotracheal device which includes a flexible, elongated tube, a primary elastic inflatable cuff positioned near the distal end of the endotracheal tube mounted on the outer surface and an inner elastic secondary furled or pleated cuff placed within the primary cuff. The primary cuff is positioned to extend longitudinally beyond said secondary cuff mounted within. The secondary cuff has a tightly furled configuration and can be inflated to the approximate diameter of the primary cuff in the event the primary cuff is ruptured or begins leaking during use. The secondary cuff, upon deflation will return to its tightly wrapped or furled position against the endotracheal tube thereby providing easy return passage of the endotracheal device from the patient when removed.

BRIEF DESCRIPTION OF THE DRAWINGS

FIG. 1 shows in perspective fashion the endotracheal device of the present invention with the primary cuff expanded and inflated;

FIGS. 2A-2D shows the secondary cuff in stages from a tightly wrapped position in 2A to a fully expanded posture in FIG. 2D;

FIG. 3 shows the cross-sectional view along lines 3—3 of FIG. 1 but with the primary cuff deflated.

DESCRIPTION OF THE PREFERRED EMBODIMENT

The preferred form of the invention is illustrated in FIG. 1 whereby an endotracheal device comprises an endotracheal tube having an inflatable primary and an inflatable furled secondary cuff thereon. The secondary cuff is formed from a resilient, stretchable synthetic polymeric material or may be formed from natural or synthetic rubber. The secondary cuff is configured in a furled fashion and due to the memory of the material from which it is formed, it will easily inflate and expand to the approximate expanded volume of the primary cuff but, upon deflation, will quickly return to its tightly wrapped and furled position around the endotracheal tube. A pair of fluid conduits are incorporated into the endotracheal tube walls and provide a means to inflate the primary and secondary cuffs. In the event the primary cuff ruptures while it is within the patient, the secondary cuff can be inflated whereby it will unfurl to the approximate volume of the inflated primary cuff to form a tight seal. When the surgical or other procedure has been completed, the inflated secondary cuff can be deflated whereby it will again resume its furled position against the endotracheal tube and will allow the tube to be easily removed from the patient. The secondary cuff is formed from a stretchable material such as synthetic rubber or other polymeric materials. Upon inflation the secondary cuff will unfurl and provide a smooth outer wall for contact with and to prevent air leakage from the trachea or other fluid leakage from the mouth.

DETAILED DESCRIPTION OF THE DRAWINGS AND OPERATION OF THE INVENTION

For a more complete understanding of the invention, turning now to the drawings, endotracheal device 10 is shown in FIG. 1 which includes endotracheal tube 11 which includes a pair of inflatable cuffs, primary cuff 12 and secondary furled cuff 13 mounted on distal end 14 of tube 11. Air is supplied to primary cuff 12 through fluid conduit 20 through connector 16 shown near the proximal end 15 of tube 11. Likewise, secondary cuff 13 is attached to fluid conduit 21 as is connector 17. Connector 16 and 17 can be joined to catheters or other air suppliers as convenient. Primary cuff 12 is attached to tube 11 by seals 18, 18' and inner or secondary furled cuff 13 is attached to tube 11 by seals 19, 19'. Conduit 20 supplies air to primary cuff 12 through openings 24 and fluid conduit 21 supplies air to secondary furled cuff 13 through openings 27.

Secondary cuff 13 is formed from a thin, resilient, stretchable materials which may be synthetic rubber or other suitable polymeric substances. As seen in FIG. 1, furled cuff 13 is tightly wrapped around tube 11 and after inflation and deflation, will return to its tightly wrapped furled posture on tube 11. FIGS. 2A through 2D demonstrate the opening or inflation of secondary cuff 13. In FIG. 2D the furled lines are totally removed thereby providing a smooth surface to form a tight seal against the trachea walls of the patient. The tightly wrapped, furled posture of cuff 13 is shown in FIG. 1 and 2A so endotracheal tube 11 can be conveniently inserted even through small nasal passages. Oftentimes, when using conventional double cuff devices, a trial inflation before surgical use of the inner cuff will result in additional bulk or diameter as the secondary cuff folds, thereby complicating the insertion of the endotracheal tube through a relatively small opening. However, with the present device, inner cuff 13, due to its furled configuration and "memory" will rapidly return upon deflation to its tightly wrapped posture.

Cuff 13 may be formed such as by molding with pleats a thin, stretchable material such as various synthetic rubbers which are commercially available and sold under a variety of trade names. Cuff 13 can be made to include a series of longitudinally extending folds or pleats 30 as seen in FIG. 2C which open upon inflation. Upon deflation pleats 30 return to their closed configuration as seen in FIG. 2A, allowing ease in removal of device 10.

In FIG. 3, both cuffs 12 and 13 are pictured in cross-sectional view in a deflated manner and the ends 25 of the furls form small ridges 26 along the outer surface of primary cuff 12. These small ridges 26 allow endotracheal device 10 to be more easily inserted since these ridges act as runners during the insertion process.

As would be understood, secondary furled cuff 13 is only inflated in the event of rupture, leak or tear of primary cuff 12. When such a rupture or tear occurs, air is forced through connector 17, down conduit 21 and into secondary cuff 13 whereupon it immediately inflates as shown in FIGS. 2A through 2D to provide an air tight or liquid seal. Once the usefulness of endotracheal device 10 has terminated, air is then allowed to escape through fluid conduit 21 whereupon secondary cuff 13 then returns to its tightly wrapped posture as shown in FIG. 2A due to the "memory" of the elastic material from which it is formed. The furled cuff configuration may also be used as the primary cuff or as the cuff in single cuff endotracheal devices.

The illustrations and examples provided herein are for explanatory purposes and are not intended to limit the scope of the appended claims.

I claim:

1. An endotracheal device comprising: an elongated tube, a primary inflatable cuff, said primary cuff mounted on said tube, a secondary inflatable furled cuff, said secondary cuff attached to said tube inside said first cuff, said secondary cuff forming a tightly wrapped configuration around said tube while deflated means for separately inflating said first and second cuffs.

2. An endotracheal device as claimed in claim 1 wherein said secondary cuff has a smooth outer surface upon inflation.

3. An endotracheal device as claimed in claim 1 wherein said secondary cuff, upon inflation expands to a volume comparable to the volume of said primary cuff, when said primary cuff is expanded.

4. An endotracheal device as claimed in claim 1 wherein said primary cuff extends longitudinally beyond said secondary cuff.

5. An endotracheal device as claimed in claim 1 and including means to inflate said cuffs.

6. An endotracheal device as claimed in claim 5 wherein said inflation means comprises a pair of fluid conduits.

7. An endotracheal device as claimed in claim 1 wherein said cuffs are formed of synthetic rubber.

8. An endotracheal device comprising: an elongated tube, a primary inflatable cuff, said primary cuff mounted on said tube, a secondary furled cuff, said secondary cuff mounted on said tube inside said primary cuff, said secondary cuff tightly wrapped around said tube, means to inflate said primary cuff, means to inflate said secondary cuff, said primary and said secondary cuff inflating means comprising fluid conduits, said fluid conduits attached to said tube.

9. An endotracheal device as claimed in claim 8 wherein said primary cuff is formed from a stretchable material.

10. An endotracheal device as claimed in claim 8 wherein said secondary cuff is formed from a synthetic material.

* * * * *